(12) United States Patent
Rao et al.

(10) Patent No.: US 7,285,692 B2
(45) Date of Patent: Oct. 23, 2007

(54) PROCESS FOR THE PREPARATION OF 1,1,1,3,3-PENTAFLUOROPROPANE AND 1,1,1,2,3-PENTAFLUOROPROPANE

(75) Inventors: Velliyur Nott Mallikarjuna Rao, Wilmington, DE (US); Allen C. Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/572,626

(22) PCT Filed: Oct. 13, 2004

(86) PCT No.: PCT/US2004/034454

§ 371 (c)(1),
(2), (4) Date: Mar. 17, 2006

(87) PCT Pub. No.: WO2005/037743

PCT Pub. Date: Apr. 28, 2005

(65) Prior Publication Data

US 2006/0217578 A1    Sep. 28, 2006

Related U.S. Application Data

(60) Provisional application No. 60/511,284, filed on Oct. 14, 2003.

(51) Int. Cl.
C07C 17/10 (2006.01)
C07C 17/00 (2006.01)
(52) U.S. Cl. .................................. 570/176; 570/175
(58) Field of Classification Search ............... 570/175, 570/176
See application file for complete search history.

(56) References Cited

U.S. PATENT DOCUMENTS

| | | | |
|---|---|---|---|
| 2,437,993 A | 3/1948 | Benning et al. | |
| 2,942,036 A | 6/1960 | Smith et al. | |
| 3,865,885 A | 2/1975 | Bruce, Jr. | |
| 3,878,257 A | 4/1975 | Bruce, Jr. | |
| 5,036,036 A | 7/1991 | Lerou | |
| 5,057,634 A | 10/1991 | Webster et al. | |
| 5,068,472 A | 11/1991 | Webster et al. | |
| 5,136,113 A | 8/1992 | Rao | |
| 5,281,568 A | 1/1994 | Scott et al. | |
| 5,396,000 A | 3/1995 | Nappa et al. | |
| 5,449,656 A | 9/1995 | Scott et al. | |
| 5,623,092 A | 4/1997 | Scott et al. | |
| 5,663,464 A | 9/1997 | Okamoto et al. | |
| 5,714,655 A | 2/1998 | Yamamoto et al. | |
| 5,945,573 A | 8/1999 | Nappa et al. | |
| 6,291,730 B1 | 9/2001 | Baker et al. | |
| 6,403,524 B2 | 6/2002 | Scott et al. | |
| 6,540,933 B1 | 4/2003 | Sievert et al. | |
| 2001/0011061 A1 | 8/2001 | Scott et al. | |

FOREIGN PATENT DOCUMENTS

| | | |
|---|---|---|
| AU | A 94/80340 | 6/1995 |
| DE | 23 58 254 | 6/1975 |
| EP | 0 502 605 | 9/1992 |
| EP | 0 657 408 | 6/1995 |
| EP | 0 703 208 | 3/1996 |
| EP | 0 982 281 | 3/2000 |
| GB | 938070 | 9/1963 |
| GB | 2 275 924 | 9/1994 |
| WO | WO98/10862 | 3/1998 |
| WO | WO2005/037431 | 4/2005 |
| WO | WO2005/037742 | 4/2005 |
| WO | WO2005/037744 | 4/2005 |

OTHER PUBLICATIONS

U.S. Appl. No. 10/572,627, filed Oct. 13, 2004, Rao et al.
U.S. Appl. No. 10/572,625, filed Oct. 13, 2004, Rao et al.
U.S. Appl. No. 10/572,628, filed Oct. 13, 2004, Amos et al.
Journal of Fluorine Chemistry, J. Kvicala et al., Preparation of Perhalogenated Chlorofluoropropanes by Halogen Exchance in the Liquid and Vapour Phases and Their Isomer Analyses by 19F NMR Spectroscopy, vol. 43 (1989), pp. 155-175.
Journal of American Chemical Soc., A.L. Henne et al., Fluorinated Derivatives of Propane and Propylene, vol. 68, (1946), pp. 496-497.

Primary Examiner—J. Parsa

(57) ABSTRACT

A process is disclosed for the manufacture of $CF_3CH_2CHF_2$ and $CF_3CHFCh_2F$. The process involves (a) reacting hydrogen fluoride, chlorine, and at least one halopropene of the formula $CX_3CCl=CClX$ (where each X is independently F or Cl) to produce a product including both $CF_3CCl_2CClF_2$ and $CF_3CClFCCl_2F$; (b) reacting $CF_3CCl_2CClF_2$ and $CF_3CClFCCl_2F$ produced in (a) with hydrogen to produce a product including both $CF_3CH_2CHF_2$, and $CF_3CHFCH_2F$; and (c) recovering $CF_3CH_2CHF_2$ and $CF_3CHFCh_2F$ from the product produced in (b). In (a), the $CF_3CCl_2CClF_2$ and $CF_3CClFCCl_2F$ are produced in the presence of a chlorofluorination catalyst including a $ZnCr_2O_4$/crystalline α-chromium oxide composition, a $ZnCr_2O_4$/crystalline α-chromium oxide composition which has been treated with a fluorinating agent, a zinc halide/α-chromium oxide composition and/or a zinc halide/α-chromuim oxide composition which has been treated with a fluorinating agent.

7 Claims, No Drawings

PROCESS FOR THE PREPARATION OF 1,1,1,3,3-PENTAFLUOROPROPANE AND 1,1,1,2,3-PENTAFLUOROPROPANE

This application represents a national filing under 35 U.S.C. 371 of PCT International Application No. PCT/US2004/034454 filed Oct. 13, 2004, and claims priority benefit of U.S. Application Ser. No. 60/511,284 filed Oct. 14, 2003.

FIELD OF THE INVENTION

This invention relates to the synthesis of 1,1,1,3,3-pentafluoro-propane and 1,1,1,2,3-pentafluoropropane.

BACKGROUND

A number of chlorine-containing halocarbons are considered to be detrimental toward the Earth's ozone layer. There is a world-wide effort to develop materials having lower ozone depletion potential that can serve as effective replacements. For example, the hydrofluorocarbon, 1,1,1,2-tetrafluoroethane (HFC-134a) is being used as a replacement for dichlorodifluoromethane (CFC-12) in refrigeration systems. There is a need for manufacturing processes that provide halogenated hydrocarbons that contain less chlorine or no chlorine. The production of hydrofluorocarbons (i.e., compounds containing only carbon, hydrogen and fluorine), has been the subject of considerable interest to provide environmentally desirable products for use as solvents, blowing agents, refrigerants, cleaning agents, aerosol propellants, heat transfer media, dielectrics, fire extinguishants and power cycle working fluids. For example, 1,1,1,3,3-pentafluoropropane has utility as a blowing agent, and 1,1,1,2,3-pentafluoropropane has utility as a refrigerant and as an intermediate for producing fluoroolefins.

SUMMARY OF THE INVENTION

This invention provides a process for the manufacture of 1,1,1,3,3-pentafluoropropane (HFC-245fa) and 1,1,1,2,3-pentafluoropropane (HFC-245eb). The process comprises (a) reacting hydrogen fluoride (HF), chlorine ($Cl_2$), and at least one halopropene of the formula $CX_3CCl=CClX$, wherein each X is independently selected from the group consisting of F and Cl, to produce a product comprising $CF_3CCl_2CClF_2$ and $CF_3CClFCCl_2F$, wherein said $CF_3CCl_2CClF_2$ and $CF_3CClFCCl_2F$ are produced in the presence of a chlorofluorination catalyst comprising at least one composition selected from the group consisting of (i) compositions comprising $ZnCr_2O_4$ and crystalline α-chromium oxide, (ii) compositions comprising a zinc halide and α-chromium oxide and (iii) compositions of (i) or (ii) which have been treated with a fluorinating agent (e.g., anhydrous hydrogen fluoride); (b) reacting $CF_3CCl_2CClF_2$ and $CF_3CClFCCl_2F$ produced in (a) with hydrogen ($H_2$), optionally in the presence of HF, to produce a product comprising $CF_3CH_2CHF_2$ and $CF_3CHFCH_2F$; and (c) recovering $CF_3CH_2CHF_2$ and $CF_3CHFCH_2F$ from the product produced in (b).

DETAILED DESCRIPTION

This invention provides a process for the preparation of $CF_3CH_2CHF_2$ (HFC-245fa) and $CF_3CHFCH_2F$ (HFC-245eb). The HFC-245fa and HFC-245eb may be recovered as individual products and/or as one or more mixtures of the two products.

In step (a) of the process of this invention, one or more halopropene compounds $CX_3CCl=CClX$, wherein each X is independently selected from the group consisting of F and Cl, are reacted with chlorine ($Cl_2$) and hydrogen fluoride (HF) to produce a product mixture comprising $CF_3CCl_2CClF_2$ (CFC-215aa) and $CF_3CClFCCl_2F$ (CFC-215bb).

Accordingly, this invention provides a process for the preparation of mixtures of $CF_3CCl_2CClF_2$ (CFC-215aa) and $CF_3CClFCCl_2F$ (CFC-215bb) from readily available starting materials.

Suitable starting materials for the process of this invention include E- and Z-$CF_3CCl=CClF$ (CFC-1214xb), $CF_3CCl=CCl_2$ (CFC-1213xa), $CClF_2CCl=CCl_2$ (CFC-1212xa), $CCl_2FCCl=CCl_2$ (CFC-1211xa), and $CCl_3CCl=CCl_2$ (hexachloropropene, HCP), or mixtures thereof.

Due to their availability, $CF_3CCl=CCl_2$ (CFC-1213xa) and $CCl_3CCl=CCl_2$ (hexachloropropene, HCP) are the preferred starting materials for the process of the invention.

Preferably, the reaction of HF and $Cl_2$ with $CX_3CCl=CClX$ is carried out in the vapor phase in a heated tubular reactor. A number of reactor configurations are possible, including vertical and horizontal orientation of the reactor and different modes of contacting the halopropene starting material(s) with HF and chlorine. Preferably the HF and chlorine are substantially anhydrous.

In one embodiment of step (a), the halopropene starting material(s) are fed to the reactor contacting the chlorofluorination catalyst. The halopropene starting material(s) may be initially vaporized and fed to the first reaction zone as gas(es).

In another embodiment of step (a), the halopropene starting material(s) may be contacted with HF in a pre-reactor. The pre-reactor may be empty (i.e., unpacked), but is preferably filled with a suitable packing such as Monel™ or Hastelloy™ nickel alloy turnings or wool, or other material inert to HCl and HF which allows efficient mixing of $CX_3CCl=CClX$ and HF vapor.

If the halopropene starting material(s) are fed to the pre-reactor as liquid(s), it is preferable for the pre-reactor to be oriented vertically with $CX_3CCl=CClX$ entering the top of the reactor and pre-heated HF vapor introduced at the bottom of the reactor.

Suitable temperatures for the pre-reactor are within the range of from about 80° C. to about 250° C., preferably from about 100° C. to about 200° C. Under these conditions, for example, hexachloropropene is converted to a mixture containing predominantly CFC-1213xa. The starting material feed rate is determined by the length and diameter of the reactor, the temperature, and the degree of fluorination desired within the pre-reactor. Slower feed rates at a given temperature will increase contact time and tend to increase the amount of conversion of the starting material and increase the degree of fluorination of the products.

The term "degree of fluorination" means the extent to which fluorine atoms replace chlorine substituents in the $CX_3CCl=CClX$ starting materials. For example, $CF_3CCl=CClF$ represents a higher degree of fluorination than $CClF_2CCl=CCl_2$ and $CF_3CCl_2CF_3$ represents a higher degree of fluorination than $CClF_2CCl_2CF_3$.

The molar ratio of HF fed to the pre-reactor, or otherwise to the reaction zone of step (a), to halopropene starting material fed in step (a), is typically from about stoichiometric to about 50:1. The stoichiometric ratio depends on the average degree of fluorination of the halopropene starting material(s) and is typically based on formation of $C_3Cl_3F_5$.

For example, if the halopropene is HCP, the stoichiometric ratio of HF to HCP is 5:1; if the halopropene is CFC-1213xa, the stoichiometric ratio of HF to CFC-1213xa is 2:1. Preferably, the molar ratio of HF to halopropene starting material is from about twice the stoichiometric ratio (based on formation of $C_3Cl_3F_5$) to about 30:1. Higher ratios of HF to halopropene are not particularly beneficial. Lower ratios result in reduced yields of $C_3Cl_3F_5$ isomers.

If the halopropene starting materials are contacted with HF in a pre-reactor, the effluent from the pre-reactor is then contacted with chlorine in the presence of a chlorofluorination catalyst.

In another embodiment of step (a), the halopropene starting material(s) may be contacted with $Cl_2$ and HF in a pre-reactor. The pre-reactor may be empty (i.e., unpacked) but is preferably filled with a suitable packing such as Monel™ or Hastelloy™ nickel alloy turnings or wool, activated carbon, or other material inert to HCl, HF, and $Cl_2$ which allows efficient mixing of $CX_3CCl\!\!=\!\!CClX$, HF, and $Cl_2$.

Typically at least a portion of the halopropene starting material(s) react(s) with $Cl_2$ and HF in the pre-reactor by addition of $Cl_2$ to the olefinic bond to give a saturated halopropane as well as by subsitution of at least a portion of the Cl substituents in the halopropropane and/or halopropene by F. Suitable temperatures for the pre-reactor in this embodiment of the invention are within the range of from about 80° C. to about 250° C., preferably from about 100° C. to about 200° C. Higher temperatures result in greater conversion of the halopropene(s) entering the reactor to saturated products and greater degrees of halogenation and fluorination in the pre-reactor products.

The term "degree of halogenation" means the extent to which hydrogen substituents in a halocarbon have been replaced by halogen and the extent to which carbon-carbon double bonds have been saturated with halogen. For example, $CF_3CCl_2CClF_2$ has a higher degree of halogenation than $CF_3CCl\!\!=\!\!CCl_2$. Also, $CF_3CCl_2CClF_2$ has a higher degree of halogenation than $CF_3CHClCClF_2$.

The molar ratio of $Cl_2$ to halopropene starting material(s) is typically from about 1:1 to about 10:1, and is preferably from about 1:1 to about 5:1. Feeding $Cl_2$ at less than a 1:1 ratio will result in the presence of relatively large amounts of unsaturated materials and hydrogen-containing side products in the reactor effluent.

In a preferred embodiment of step (a) the halopropene starting materials are vaporized, preferably in the presence of HF, and contacted with HF and $Cl_2$ in a pre-reactor and then contacted with the chlorofluorination catalyst. If the preferred amounts of HF and $Cl_2$ are fed in the pre-reactor, additional HF and $Cl_2$ are not required when the effluent from the pre-reactor contacts the chlorofluorination catalyst.

Suitable temperatures for catalytic chlorofluorination of halopropene starting material and/or their products formed in the pre-reactor are within the range of from about 200° C. to about 400° C., preferably from about 250° C. to about 350° C., depending on the desired conversion of the starting material and the activity of the catalyst. Reactor temperatures greater than about 350° C. may result in products having a degree of fluorination greater than five. In other words, at higher temperatures, substantial amounts of chloropropanes containing six or more fluorine substituents (e.g., $CF_3CCl_2CF_3$ or $CF_3CClFCClF_2$) may be formed. Reactor temperature below about 240° C. may result in a substantial yield of products with a degree of fluorination less than five (i.e., underfluorinates).

Suitable reactor pressures for vapor phase embodiments of this invention may be in the range of from about 1 to about 30 atmospheres. Reactor pressures of about 5 atmospheres to about 20 atmospheres may be advantageously employed to facilitate separation of HCl from other reaction products in step (b) of the process.

The chlorofluorination catalysts which are used in the process of the present invention are preferably compositions comprising $ZnCr_2O_4$ (zinc chromite) and crystalline α-$Cr_2O_3$ (alpha chromium oxide) or compositions obtained by treatment of said compositions comprising $ZnCr_2O_4$ (zinc chromite) and α-$Cr_2O_3$ (alpha chromium oxide) with a fluorinating agent. The amount of zinc relative to the total of chromium and zinc in these compositions is preferably from about 1 atom % to about 25 atom %.

Of note are chromium-containing catalyst compositions comprising $ZnCr_2O_4$ (zinc chromite) and crystalline α-chromium oxide wherein the $ZnCr_2O_4$ contains between about 10 atom percent and 67 atom percent of the chromium in the composition and at least about 70 atom percent of the zinc in the composition, and wherein at least about 90 atom percent of the chromium present as chromium oxide in the composition is present as $ZnCr_2O_4$ or crystalline α-chromium oxide. Also of note are chromium-containing catalyst compositions, prepared by treatment of such compositions comprising $ZnCr_2O_4$ and crystalline α-chromium oxide with a fluorinating agent. Also of note are such chromium-containing catalyst compositions which comprise $ZnCr_2O_4$ and crystalline α-chromium oxide wherein the $ZnCr_2O_4$ contains between about 20 atom percent and about 50 atom percent of the chromium in the composition. Also of note are such chromium-containing catalyst compositions which comprise $ZnCr_2O_4$ and crystalline α-chromium oxide wherein the $ZnCr_2O_4$ contains at least about 90 atom percent of the zinc in the composition. Also of note are such chromium-containing catalyst compositions comprising zinc chromite and crystalline α-chromium oxide wherein greater than 95 atom percent of the chromium that is not present as zinc chromite is present as crystalline α-chromium oxide. Also of note are such chromium-containing catalyst compositions which consist essentially of $ZnCr_2O_4$ (zinc chromite) and crystalline α-chromium oxide.

These compositions may be prepared, for example, by co-precipitation methods followed by calcination.

In a typical co-precipitation procedure, an aqueous solution of zinc and chromium(III) salts is prepared. The relative concentrations of the zinc and chromium(III) salts in the aqueous solution is dictated by the bulk atom percent zinc relative to chromium desired in the final catalyst. Therefore, the concentration of zinc in the aqueous solution is from about 1 mole % to about 25 mole % of the total concentration of zinc and chromium in the solution. The concentration of chromium (III) in the aqueous solution is typically in the range of 0.3 to 3 moles per liter with 0.75-1.5 moles per liter being a preferred concentration. While different chromium (III) salts might be employed, chromium(III) nitrate or its hydrated forms such as $[Cr(NO_3)_3(H_2O)_9]$, are the most preferred chromium(III) salts for preparation of said aqueous solution.

While different zinc salts might be employed for preparation of said aqueous solutions, preferred zinc salts for preparation of catalysts for the process of this invention include zinc(II) nitrate and its hydrated forms such as $[Zn(NO_3)_2(H_2O)_6]$.

The aqueous solution of the chromium (III) and zinc salts may then be evaporated either under vacuum or at elevated temperature to give a solid which is then calcined.

It is preferred to treat the aqueous solution of the chromium(III) and zinc salts with a base such as ammonium hydroxide (aqueous ammonia) to precipitate the zinc and chromium as the hydroxides. Bases containing alkali metals such as sodium or potassium hydroxide or the carbonates may be used but are not preferred. The addition of ammonium hydroxide to the aqueous solution of the chromium (III) and zinc salts is typically carried out gradually over a period of 1 to 12 hours. The pH of the solution is monitored during the addition of base. The final pH is typically in the range of 6.0 to 11.0, preferably from about 7.5 to about 9.0, most preferably about 8.0 to about 8.7. The precipitation of the zinc and chromium hydroxide mixture is typically carried out at a temperature of about 15° C. to about 60° C., preferably from about 20° C. to about 40° C. After the ammonium hydroxide is added, the mixture is typically stirred for up to 24 hours. The precipitated chromium and zinc hydroxides serve as precursors to $ZnCr_2O_4$ and $\alpha$-chromium oxide.

After the precipitation of the zinc and chromium hydroxide mixture is complete, the mixture is dried by evaporation. This may be carried out by heating the mixture in an open pan on a hot plate or steam bath or in an oven or furnace at a suitable temperature. Suitable temperatures include temperatures from about 60° C. to about 130° C. (for example, about 100° C. to about 120° C.). Alternatively the drying step may be carried out under vacuum using, for example, a rotary evaporator.

Optionally, the precipitated zinc and chromium hydroxide mixture may be collected and, if desired, washed with deionized water before drying. Preferably the precipitated zinc and chromium hydroxide mixture is not washed prior to the drying step.

After the zinc and chromium hydroxide mixture has been dried, the nitrate salts are then decomposed by heating the solid from about 250° C. to about 350° C. The resulting solid is then calcined at temperatures of from about 400° C. to about 1000° C., preferably from about 400° C. to about 900° C.

Further information on the zinc and chromium compositions useful for this invention is provided in U.S. patent application No. 60/511,353 [CL2244 US PRV] filed Oct. 14, 2003, and hereby incorporated by reference herein in its entirety (see also corresponding International Application No. PCT/US2004/034446).

The calcined zinc chromite/$\alpha$-chromium oxide compositions of the present invention may be pressed into various shapes such as pellets for use in packing reactors. It may also be used in powder form.

Typically, the calcined compositions will be pre-treated with a fluorinating agent prior to use as catalysts for changing the fluorine content of halogenated carbon compounds. Typically this fluorinating agent is HF though other materials may be used such as sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pretreatment is not essential.

Other catalysts suitable for the chlorofluorinations of step (a) are compositions comprising a zinc halide and $\alpha$-chromium oxide and compositions obtained by treatment of said compositions comprising a zinc halide and $\alpha$-chromium oxide with a fluorinating agent. U.S. Pat. No. 3,878,257 discloses an example of such catalysts. The amount of zinc relative to the total of chromium and zinc in these compositions is preferably from about 0.1 atom % to about 25 atom %; and is more preferably from about 2 atom % to about 10 atom %. Of note are compositions wherein a zinc halide is supported on a support comprising $\alpha$-chromium oxide. Preferably, the $\alpha$-chromium oxide is prepared according to U.S. Pat. No. 5,036,036. Pretreatment with a fluorinating agent can be carried out as indicated above for the calcined zinc chromite/$\alpha$-chromium oxide compositions.

Compounds that are produced in the chlorofluorination process in step (a) include the halopropanes $CF_3CCl_2CClF_2$ (CFC-215aa) and $CF_3CClFCCl_2F$ (CFC-215bb).

Halopropane by-products that have a higher degree of fluorination than CFC-215aa and CFC-215bb that may be produced in step (a) include $CF_3CCl_2CF_3$ (CFC-216aa), $CF_3CClFCClF_2$ (CFC-216ba), $CF_3CF_2CCl_2F$ (CFC-216cb), $CF_3CClFCF_3$ (CFC-217ba), and $CF_3CHClCF_3$ (HCFC-226da).

Halopropane by-products that may be formed in step (a) which have lower degrees of fluorination than CFC-215aa and CFC-215bb include $CF_3CCl_2CCl_2F$ (HCFC-214ab).

Halopropene by-products that may be formed in step (a) include $CF_3CCl=CF_2$ (CFC-1215xc), E- and Z-$CF_3CCl=CClF$ (CFC-1214xb), and $CF_3CCl=CCl_2$ (CFC-1213xa).

Typically the effluent from step (a) comprising $CF_3CCl_2CClF_2$ (CFC-215aa) and $CF_3CClFCCl_2F$ (CFC-215bb), and optionally HF, is separated from lower boiling components comprising HCl, $Cl_2$, HF, over-fluorinated products comprising $C_3ClF_7$ and $C_3Cl_2F_6$ isomers, the under-halogenated components comprising $C_3ClF_5$ and $C_3Cl_2F_4$ isomers, and the under-fluorinated components comprising $C_3Cl_4F_4$ isomers and CFC-1213xa.

In one embodiment of the invention the reactor effluent from step (a) may be delivered to a distillation column in which HCl and any HCl azeotropes are removed from the top of column while the higher boiling components are removed at the bottom of the column. The products recovered at the bottom of the first distillation column are then delivered to a second distillation column in which HF, $Cl_2$, $CF_3CCl_2CF_3$ (CFC-216aa), $CF_3CClFCClF_2$ (CFC-216ba), $CF_3CF_2CCl_2F$ (CFC-216cb), $CF_3CClFCF_3$ (CFC-217ba), and $CF_3CHClCF_3$ (HCFC-226da) and their HF azeotropes are recovered at the top of the column and CFC-215aa and CFC-215bb, and any remaining HF and the higher boiling components are removed from the bottom of the column. The products recovered from the bottom of the second distillation column may then be delivered to a further distillation columns to separate the under-fluorinated by-products and intermediates and to isolate CFC-215aa and CFC-215bb.

Optionally, after distillation and separation of HCl from the reactor effluent of step (a), the resulting mixture of HF and halopropanes and halopropenes may be delivered to a decanter controlled at a suitable temperature to permit separation of a liquid HF-rich phase and a liquid organic-rich phase. The organic-rich phase may then be distilled to isolate the CFC-215aa and CFC-215bb. The HF-rich phase may then be recycled to the reactor of step (a), optionally after removal of any organic components by distillation. The decantation step may be used at other points in the CFC-215aa/CFC-215bb separation scheme where HF is present.

In one embodiment of the present invention said underfluorinated and underhalogenated components (e.g., CFC-214ab, CFC-1212xb, and CFC-1213xa) are returned to step (a).

In another embodiment of the present invention, the CFC-216aa, CFC-216ba and HCFC-226da by-products are further reacted with HF, or if HCFC-226da is present, HF and $Cl_2$, to give $CF_3CClFCF_3$ (CFC-217ba) which in turn may be converted to hexafluoropropene (HFP) as disclosed in U.S. Pat. Nos. 5,068,472 and 5,057,634.

In another embodiment of the present invention, the HCFC-226da, CFC-216aa, CFC-216ba, CFC-217ba, and by-products are further reacted with hydrogen ($H_2$) to give 1,1,1,3,3,3-hexafluoropropane (HFC-236fa), 1,1,1,2,3,3-hexafluoropropane (HFC-236ea), and 1,1,1,2,3,3,3-heptafluoropropane (HFC-227ea) as disclosed in U.S. patent application No. 60/511,355 [CL2246 US PRV] filed Oct. 14, 2003 (see also corresponding International Application No. PCT/US2004/034447).

In step (b) of the process of this invention, $CF_3CCl_2CClF_2$ (CFC-215aa) and $CF_3CClFCCl_2F$ (CFC-215bb) produced in step (a) are reacted with hydrogen ($H_2$), optionally in the presence of HF.

In one embodiment of step (b), a mixture comprising CFC-215aa and CFC-215bb is delivered in the vapor phase, along with hydrogen ($H_2$), and optionally HF, to a reactor fabricated from nickel, iron, titanium, or their alloys, as described in U.S. Pat. No. 6,540,933; the teachings of this disclosure are incorporated herein by reference. A reaction vessel of these materials (e.g., a metal tube) optionally packed with the metal in suitable form may also be used. When reference is made to alloys, it is meant a nickel alloy containing form 1 to 99.9% (by weight) nickel, an iron alloy containing 0.2 to 99.8% (by weight) iron, and a titanium alloy containing 72-99.8% (by weight) titanium. Of note is use of an empty (i.e., unpacked) reaction vessel made of nickel or alloys of nickel such as those containing 40% to 80% nickel, e.g., Inconel™ 600 nickel alloy, Hastelloy™ C617 nickel alloy, or Hastelloy™ C276 nickel alloy.

When used for packing, the metal or metal alloys may be particles or formed shapes such as perforated plates, rings, wire, screen, chips, pipe, shot, gauze, or wool.

The temperature of the reaction in this embodiment can be between about 350° C. and about 600° C., and is preferably at least about 450° C.

The molar ratio of hydrogen to the CFC-215aa/CFC-215bb mixture fed to the reaction zone should be in the range of about 0.1 mole $H_2$ per mole of CFC-215 isomer to about 60 moles of $H_2$ per mole of CFC-215 isomer, more preferably from about 0.4 to 10 moles of $H_2$ per mole of CFC-215 isomer.

In another embodiment of step (b), the contacting of hydrogen with CFC-215aa and CFC-215bb produced in step (a), and optionally HF, is carried out in the presence of a hydrogenation catalyst. Hydrogenation catalysts suitable for use in this embodiment include catalysts comprising at least one metal selected from the group consisting of rhenium, iron, ruthenium, osmium, cobalt, rhodium, iridium, nickel, palladium, and platinum. Said catalytic metal component is typically supported on a carrier such as carbon or graphite or a metal oxide, fluorinated metal oxide, or metal fluoride where the carrier metal is selected from the group consisting of magnesium, aluminum, titanium, vanadium, chromium, iron, and lanthanum. Of note are carbon supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference.

The supported metal catalysts may be prepared by conventional methods known in the art such as by impregnation of the carrier with a soluble salt of the catalytic metal (e.g., palladium chloride or rhodium nitrate) as described by Satterfield on page 95 of *Heterogenous Catalysis in Industral Practice*, 2nd edition (McGraw-Hill, New York, 1991). The concentration of the catalytic metal(s) on the support is typically in the range of about 0.1% by weight of the catalyst to about 5% by weight.

The relative amount of hydrogen contacted with CFC-215aa and CFC-215bb in the presence of a hydrogenation catalyst is typically from about 0.5 mole of $H_2$ per mole of trichloropentafluoropropane isomer to about 10 moles of $H_2$ per mole of trichloropentafluoropropane isomer, preferably from about 3 moles of $H_2$ per mole of trichloropentafluoropropane isomer to about 8 moles of $H_2$ per mole of trichloropentafluoropropane isomer.

Suitable temperatures for the catalytic hydrogenation are typically in the range of from about 100° C. to about 350° C., preferably from about 125° C. to about 300° C. Temperatures above about 350° C. tend to result in defluorination side reactions; temperatures below about 125° C. will result in incomplete substitution of Cl for H in the $C_3Cl_3F_5$ starting materials.

The reactions are typically conducted at atmospheric pressure or superatmospheric pressure.

The effluent from the step (b) reaction zone typically includes HCl, unreacted hydrogen, $CF_3CH_2CHF_2$ (HFC-245fa), $CF_3CHFCH_2F$ (HFC-245eb), lower boiling by-products (typically including $CF_3CH=CF_2$ (HFC-1225zc), E- and Z-$CF_3CH=CHF$ (HFC-1234ze), $CF_3CF=CH_2$ (HFC-1234yf), $CF_3CH_2CF_3$ (HFC-236fa), $CF_3CHFCH_3$ (HFC-254eb), and/or $CF_3CH_2CH_3$ (HFC-263fb)) and higher boiling by-products and intermediates (typically including $CF_3CH_2CH_2Cl$ (HCFC-253fb), $CF_3CHFCH_2Cl$ (HCFC-244eb), $CF_3CClFCH_2F$ (HCFC-235bb), $CF_3CHClCHF_2$ (HCFC-235da), $CF_3CHClCClF_2$ (HCFC-225da), and/or $CF_3CClFCHClF$ (HCFC-225ba diastereromers)) as well as any HF carried over from step (a) or step (b).

In step (c), the desired products are recovered. The reactor products from step (b) may be delivered to a separation unit to recover $CF_3CH_2CHF_2$ and $CF_3CHFCH_2F$, individually or as a mixture.

Partially chlorinated components such as HCFC-235da, HCFC-235bb, HCFC-225ba, and HCFC-225da may also be recovered and recycled back to step (b).

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific embodiments are to be construed as merely illustrative, and do not constrain the remainder of the disclosure in any way whatsoever.

EXAMPLES

LEGEND

| | |
|---|---|
| 214ab is $CF_3CCl_2CCl_2F$ | 215aa is $CF_3CCl_2CClF_2$ |
| 215bb is $CCl_2FCClFCF_3$ | 216aa is $CF_3CCl_2CF_3$ |
| 216ba is $CClF_2CClFCF_3$ | 217ba is $CF_3CClFCF_3$ |
| 225ba is $CF_3CClFCHClF$ | 225da is $CF_3CHClCClF_2$ |
| 226da is $CF_3CHClCF_3$ | 235bb is $CF_3CClFCH_2F$ |
| 235 is $C_3H_2ClF_5$ | 235da is $CF_3CHClCHF_2$ |
| 235fa is $CF_3CH_2CClF_2$ | 236fa is $CF_3CH_2CF_3$ |
| 245eb is $CF_3CHFCH_2F$ | 245fa is $CF_3CH_2CHF_2$ |
| 254eb is $CF_3CHFCH_3$ | 263fb is $CF_3CH_2CH_3$ |
| 1213xa is $CF_3CCl=CCl_2$ | 1215xc is $CF_3CCl=CF_2$ |
| 1224 is $C_3HClF_4$ | 1225zc is $CF_3CH=CF_2$ |

Catalyst Preparation

Comparative Preparation Example 1

Preparation of 100% Chromium Catalyst (400° C.)

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The dried solid was then calcined in air at 400° C.; the resulting solid weighed 61.15 g. The catalyst was pelletized (−12 to +20 mesh (1.68 to 0.84 mm)) and 28.2 g (20 mL) was used in Comparative Example 3.

Comparative Preparation Example 2

Preparation of 2% Zinc on Alumina Catalyst

Aluminum oxide (4.90 moles, Harshaw 3945, dried at 110° C.) was added to a solution of 20.85 g $ZnCl_2$ (0.153 mole) dissolved in 460 mL of distilled water. Water was evaporated from the mixture with stirring and then dried at 110° C. for three days. The catalyst was pelletized (−12 to +20 mesh (1.68 to 0.84 mm)) and 21.1 g (30 mL) was used in Comparative Example 1.

Preparation Example 1

Preparation of 2% Zinc chloride supported on Chromium oxide

A solution of 1.20 g $ZnCl_2$ (8.81 mmoles) in 60 mL of deionized water contained in a 125 mm×65 mm glass dish was treated with 60.00 g (0.357 mole) of 12-20 mesh $Cr_2O_3$. The dish was placed on a warm hot plate and the slurry allowed to dry with occasional stirring. The resulting solid was then dried overnight at 130° C.; the resulting solid weighed 60.42 g. The catalyst was pelletized (−12 to +20 mesh (1.68 to 0.84 mm)) and 41.5 g (30 mL) was used in Example 9.

Preparation Example 2

Preparation of 95% Chromium/5% Zinc Catalyst (450° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 450° C. for 20 hours; the resulting solid weighed 76.72 g.

The catalyst was pelletized (−12 to +20 mesh (1.68 to 0.84 mm)) and 38.5 g (25 mL) was used in Example 13.

Preparation Example 3

Preparation of 90% Chromium/10% Zinc Catalyst (900° C.)

A solution of 360.13 g $Cr(NO_3)_3[9(H_2O)]$ (0.900 mole) and 29.75 g $Zn(NO_3)_2[6(H_2O)]$ (0.100 mole) was prepared in 1000 mL of deionized water. The solution was treated with 450 mL of 7.4M aqueous ammonium hydroxide over the course of 1.4 hours; the pH increased from 1.9 to pH 8.4. The slurry was stirred at room temperature overnight and then dried at 120° C. in the presence of air. The dried solid was then calcined in air at 900° C. for 20 hours; the resulting solid weighed 75.42 g. The catalyst was pelletized (−12 to +20 mesh (1.68 to 0.84 mm)) and 42.3 g (25 mL) was used in Examples 4, 5, and 6.

Preparation Example 4

Preparation of 95% Chromium/5% Zinc Catalyst (900° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 900° C. for 20 hours; the resulting solid weighed 70.06 g. The catalyst was pelletized (−12 to +20 mesh (1.68 to 0.84 mm)) and 25.3 g (14 mL) was used in Examples 1 and 2.

Preparation Example 5

Preparation of 98% Chromium/2% Zinc Catalyst (900° C.)

A solution of 392.15 g $Cr(NO_3)_3[9(H_2O)]$ (0.980 mole) and 5.94 g $Zn(NO_3)_2[6(H_2O)]$ (0.020 mole) was prepared in 1000 mL of deionized water. The solution was treated with 450 mL of 7.4M aqueous ammonium hydroxide over the course of 0.58 hour; the pH increased from 1.67 to pH 8.35. The slurry was stirred at room temperature overnight and then dried at 120° C. in an oven in the presence of air. The dried solid was then calcined in air at 900° C. for 21 hours; the resulting solid weighed 66.00 g. The catalyst was pelletized (−12 to +20 mesh (1.68 to 0.84 mm)) and 44.9 g (23 mL) was used in Examples 7 and 8.

Preparation Example 6

Preparation of 10% Zinc chloride supported on Chromium oxide

A solution of 6.0 g ZnCl$_2$ (44 mmoles) in 300 mL of deionized water contained in a 170 mm×90 mm glass dish was treated with 60.00 g (0.357 mole) of 12-20 mesh Cr$_2$O$_3$. The dish was placed on a warm hot plate and the slurry allowed to dry with occasional stirring. The resulting solid was then dried overnight at 130° C.; the resulting solid weighed 65.02 g. The catalyst was pelletized (−12 to +20 mesh (1.68 to 0.84 mm)) and 37.5 g (25 mL) was used in Examples 10 and 11.

Preparation Example 7

Preparation of 98.1% Chromium/1.9% Zinc Catalyst (550° C.)

A solution of 516.46 g Cr(NO$_3$)$_3$[9(H$_2$O)] (1.29 moles) and 7.31 g Zn(NO$_3$)$_2$[6(H$_2$O)] (0.0246 mole) was prepared in 500 mL of distilled water in 1 L beaker resting on a hot plate. The mixture was then transferred to a Pyrex™ container and the container placed in a furnace. The container was heated from room temperature to 125° C. at 10° C./min and then held at 125° C. for six hours. The container was heated from 125° C. to 350° C. at 1° C./min and then held at 350° C. for six hours. The container was heated from 350° C. to 550° C. at 1° C./min and then held at 550° C. for 24 hours. The catalyst was pelletized (−12 to +20 mesh (1.68 to 0.84 mm)) and 29.9 g (20 mL) was used in Example 12.

Preparation Example 8

Preparation of 80% Chromium/20% Zinc Catalyst (900° C.)

A solution of 320.12 g of Cr(NO$_3$)$_3$[9(H$_2$O)] (0.800 mole) and 59.49 g Zn(NO$_3$)$_2$[6(H$_2$O)] (0.200 mole) was prepared in 1000 mL of deionized water. The solution was treated with 450 mL of 7.4M aqueous ammonium hydroxide over the course of one hour; the pH increased from about 1.7 to about pH 8.4. The slurry was stirred at room temperature overnight and then dried at 120° C. in an oven in the presence of air. The dried solid was then calcined in air at 900° C. for 22 hours; the resulting solid weighed 75.80 g. The catalyst was pelletized (−12 to +20 mesh, (1.68 to 0.84 mm)) and 41.7 g (25 mL) was used in Example 3.

Examples 1-13 and Comparative Examples 14

General Procedure for Chlorofluorination

A weighed quantity of pelletized catalyst was placed in a ⅝" (1.58 cm) diameter Inconel™ nickel alloy reactor tube heated in a fluidized sand bath. The tube was heated from 50° C. to 175° C. in a flow of nitrogen (50 cc/min; 8.3(10)$^{-7}$ m$^3$/sec) over the course of about one hour. HF was then admitted to the reactor at a flow rate of 50 cc/min (8.3(10)$^{-7}$ m$^3$/sec). After 0.5 to 2 hours the nitrogen flow was decreased to 20 cc/min (3.3(10)$^{-7}$ m$^3$/sec) and the HF flow increased to 80 cc/min (1.3(10)$^{-6}$ m$^3$/sec); this flow was maintained for about 1 hour. The reactor temperature was then gradually increased to 400° C. over 3 to 5 hours. At the end of this period, the HF flow was stopped and the reactor cooled to 300° C. under 20 sccm (3.3(10)$^{-7}$ m$^3$sec) nitrogen flow. CFC-1213xa was fed from a pump to a vaporizer maintained at about 118° C. The CFC-1213xa vapor was combined with the appropriate molar ratios of HF and Cl$_2$ in a 0.5 inch (1.27 cm) diameter Monel™ nickel alloy tube packed with Monel™ turnings. The mixture of reactants then entered the reactor; the contact time was 30 seconds unless otherwise indicated. All reactions were conducted at a nominal pressure of one atmosphere. The results of CFC-1213xa chlorofluorination over the several catalysts are shown in Table 1; analytical data is given in units of GC area %.

Examples 14-17

Hydrodechlorination of CF$_3$CCl$_2$CClF$_2$

The results of the hydrodechlorination of a mixture of CF$_3$CCl$_2$CClF$_2$ over a 0.5% Pd supported on carbon catalyst are shown in Table 2. The product analytical data is given in units of GC area %. The nominal catalyst bed volume was 15 mL; the contact time was 30 seconds. Prior to beginning the hydrodechlorination, the catalyst was reduced in a stream of hydrogen at 300° C.

Examples 18-19

Hydrodechlorination of CF$_3$CClFCCl$_2$F

The results of the hydrodechlorination of CF$_3$CClFCCl$_2$F over the 0.5% Pd on carbon catalyst used in Examples 14-17 are shown in Table 3. The product analytical data is given in units of GC area percent.

TABLE 1

| EX. NO. | HF:1213:Cl$_2$ | T° C. | Cat. | 1215xc | 217ba | 226da | 216aa | 216ba | 215aa | 215bb | 214ab |
|---|---|---|---|---|---|---|---|---|---|---|---|
| 1 | 30:1:10 | 280 | Cr/Zn 95/5 900° C. | 0.03 | 4.7 | 0.1 | 7.2 | 13.1 | 42.6 | 27.1 | 3.3 |
| 2 | 30:1:10 | 320 | Cr/Zn 95/5 900° C. | 0.05 | 7.5 | 0.2 | 16.2 | 18.4 | 33.5 | 21.7 | 0.5 |
| 3 | 20:1:4 | 280 | Cr/Zn 80/20 900° C. | 1.6 | 0.3 | 0.4 | 11.0 | 10.5 | 34.8 | 38.6 | 1.0 |
| 4 | 20:1:4 | 280 | Cr/Zn 90/10 900° C. | 0.3 | 0.4 | 0.8 | 15.5 | 4.3 | 53.1 | 30.2 | 4.0 |
| 5 | 20:1:4 | 300 | Cr/Zn 90/10 900° C. | 0.3 | 0.6 | 1.0 | 21.8 | 8.6 | 52.4 | 13.8 | 0.2 |
| 6 | 30:1:10 | 300 | Cr/Zn 90/10 900° C. | 0.1 | 0.8 | 0.5 | 16.9 | 10.3 | 54.9 | 15.2 | 0.2 |
| 7 | 20:1:4 | 280 | Cr/Zn 98/2 900° C. | 0.2 | 3.7 | 0.7 | 15.3 | 2.7 | 41.2 | 16.8 | 18.0 |
| 8 | 20:1:4 | 330 | Cr/Zn 98/2 900° C. | 0.1 | 11.2 | 0.5 | 28.0 | 22.7 | 28.9 | 6.6 | 0.03 |
| 9 | 20:1:4 | 260 | Cr/ZnCl$_2$ 2% | 0.6 | 0.9 | 0.8 | 9.0 | 3.7 | 75.9 | 7.3 | 0.8 |
| 10 | 20:1:4 | 280 | Cr/ZnCl$_2$ 10% | — | — | — | 4.7 | — | 24.9 | 18.3 | 50.8 |
| 11 | 20:1:4 | 320 | Cr/ZnCl$_2$ 10% | 0.3 | 0.2 | 0.1 | 10.8 | 3.9 | 47.4 | 26.0 | 9.5 |
| 12$^a$ | 20:1:4 | 300 | Cr/Zn 98/2 550° C. | 1.6 | 6.8 | 1.3 | 24.1 | 10.2 | 39.2 | 14.8 | 0.5 |
| 13 | 20:1:4 | 280 | Cr/Zn 95/5 450° C. | 0.3 | 0.1 | 1.8 | 10.2 | 3.4 | 77.7 | 5.0 | 0.3 |

TABLE 1-continued

| EX. NO. | HF:1213:Cl$_2$ | T° C. | Cat. | 1215xc | 217ba | 226da | 216aa | 216ba | 215aa | 215bb | 214ab |
|---|---|---|---|---|---|---|---|---|---|---|---|
| Comp. Ex. 1 | 20:1:4 | 280 | Zn/Al$_2$O$_3$ | 0.5 | — | 29.1 | 4.0 | 0.3 | 65.3 | — | 0.05 |
| Comp. Ex. 2$^c$ | 20:1:4 | 300 | Cr$_2$O$_3$ 900° C. | 0.6 | 5.9 | 0.3 | 22.5 | 15.4 | 26.8 | 25.8 | 0.2 |
| Comp. Ex. 3$^a$ | 20:1:4 | 320 | Cr$_2$O$_3$ | 0.2 | 12.4 | 2.4 | 30.3 | 18.0 | 34.5 | — | 0.02 |
| Comp. Ex. 4$^d$ | 20:1:4 | 300 | Cr$_2$O$_3$ HSA | 0.9 | 0.1 | 11.7 | 25.9 | 1.6 | 59.2 | — | — |

$^a$The contact time was 15 seconds.
$^b$The contact time was 5 seconds.
$^c$Catalyst prepared by pyrolysis of ammonium dichromate and calcined at 900° C. (see U.S. Pat. No. 5,036,036). Pre-treated with HF according to the general procedure.
$^d$High surface area chromium oxide obtained from a commercial source. Pre-treated with HF according to the general procedure.

TABLE 2

| EX. NO. | H$_2$:215aa | T° C. | CH$_4$ C$_2$H$_6$ C$_3$H$_8$ | 226da | 263fb | 1225zc | 236fa | 245fa | 1215xc | 235fa | 235da | 1224 | 225da | 215aa |
|---|---|---|---|---|---|---|---|---|---|---|---|---|---|---|
| 14 | 4:1 | 100 | 0.02 | 0.5 | — | 63.1 | — | 9.5 | 3.9 | 0.3 | 4.8 | 0.3 | 16.6 | 0.05 |
| 15 | 6:1 | 175 | 0.02 | 0.4 | — | 0.4 | — | 90.3 | 0.01 | 3.4 | 5.3 | — | 0.08 | — |
| 16 | 6:1 | 225 | 0.03 | 0.03 | 0.2 | — | 0.2 | 97.2 | 0.01 | 1.9 | — | — | — | — |
| 17 | 6:1 | 275 | 0.07 | — | 1.1 | 0.1 | 0.2 | 95.8 | 0.01 | 1.5 | — | — | — | — |

TABLE 3

| EX. NO. | H$_2$:215bb | T° C. | 226da | 254eb | 235 | 245eb | 235bb | 225ba | 215bb |
|---|---|---|---|---|---|---|---|---|---|
| 18 | 6:1 | 175 | 0.2 | 8.5 | 1.2 | 82.3 | 5.8 | 2.0 | — |
| 19 | 61 | 225 | 0.6 | 10.7 | 1.4 | 87.2 | 0.1 | 0.1 | — |

What is claimed is:

1. A process for the manufacture of 1,1,1,3,3-pentafluoropropane and 1,1,1,2,3-pentafluoropropane, comprising:
   (a) reacting hydrogen fluoride, chlorine, and at least one halopropene of the formula CX$_3$CCl=CCIX, wherein each X is independently selected from the group consisting of F and Cl, to produce a product comprising CF$_3$CCl$_2$CClF$_2$ and CF$_3$CClFCCl$_2$F, wherein said CF$_3$CCl$_2$CClF$_2$ and CF$_3$CClFCCl$_2$F are produced in the presence of a chlorofluorination catalyst comprising at least one composition selected from the group consisting of (i) compositions comprising ZnCr$_2$O$_4$ and crystalline α-chromium oxide, (ii) compositions comprising a zinc halide and α-chromium oxide and (iii) compositions of (i) or (ii) which have been treated with a fluorinating agent;
   (b) reacting CF$_3$CCl$_2$CClF$_2$ and CF$_3$CClFCCl$_2$F produced in (a) with hydrogen to produce a product comprising CF$_3$CH$_2$CHF$_2$ and CF$_3$CHFCH$_2$F; and
   (c) recovering CF$_3$CH$_2$CHF$_2$ and CF$_3$CHFCH$_2$F from the product produced in (b).

2. The process of claim 1 wherein in (a) the catalyst is selected from the group consisting of (i) compositions comprising ZnCr$_2$O$_4$ and crystalline α-chromium oxide and (iii) compositions of (i) which have been treated with a fluorinating agent.

3. The process of claim 2 wherein the amount of zinc relative to the total of chromium and zinc in the catalyst composition is from about 1 atom % to about 25 atom %.

4. The process of claim 2 wherein the catalyst is selected from the group consisting of (i) compositions comprising ZnCr$_2$O$_4$ and crystalline α-chromium oxide wherein the ZnCr$_2$O$_4$ contains between about 10 atom percent and 67 atom percent of the chromium in the composition and at least about 70 atom percent of the zinc in the composition, and wherein at least about 90 atom percent of the chromium present as chromium oxide in the composition is present as ZnCr$_2$O$_4$ or crystalline α-chromium oxide and (iii) compositions of (i) which have been treated with a fluorinating agent.

5. The process of claim 1 wherein in (a) the catalyst is selected from the group consisting of (ii) compositions comprising a zinc halide and α-chromium oxide and (iii) compositions of (ii) which have been treated with a fluorinating agent.

6. The process of claim 5 wherein the amount of zinc relative to the total of chromium and zinc in the catalyst composition is from about 0.1 atom % to about 25 atom %.

7. The process of claim 5 wherein the catalyst is selected from the group consisting of (ii) compositions wherein a zinc halide is supported on a support comprising α-chromium oxide and (iii) compositions of (ii) which have been treated with a fluorinating agent; and wherein the amount of zinc relative to the total of chromium and zinc in the catalyst composition is from about 2 atom % to about 10 atom %.

* * * * *